US00PP33728P2

(12) United States Plant Patent
Barends

(10) Patent No.: US PP33,728 P2
(45) Date of Patent: Dec. 7, 2021

(54) ***PELARGONIUM* PLANT NAMED 'DOPELBEZSAL'**

(50) Latin Name: ***Pelargonium zonale* X *Pelargonium peltatum***
Varietal Denomination: Dopelbezsal

(71) Applicant: DUMMEN GROUP B.V., De Lier (NL)

(72) Inventor: Eveline Barends, De Lier (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/242,222

(22) Filed: Apr. 27, 2021

(51) Int. Cl.
*A01H 6/42* (2018.01)
*A01H 5/02* (2018.01)

(52) U.S. Cl.
USPC ..... Plt./328

(58) Field of Classification Search
USPC ..... Plt./328
See application file for complete search history.

(56) References Cited

PUBLICATIONS

PLUTO Plant Variety Database Jul. 28, 2021. p. 1.*

* cited by examiner

*Primary Examiner* — Annette H Para
(74) *Attorney, Agent, or Firm* — C. Anne Whealy

(57) ABSTRACT

A new and distinct cultivar of *Pelargonium* plant named 'Dopelbezsal', characterized by its upright and rounded plant habit; vigorous growth habit; freely basal branching habit; dark green-colored leaves; early and freely flowering habit; large salmon pink-colored flowers; and good garden performance and high temperature tolerance.

1 Drawing Sheet

Botanical designation: *Pelargonium zonale* X *Pelargonium peltatum.*

Cultivar denomination: 'DOPELBEZSAL'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Dec. 2, 2020, application number 2020/3153. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Pelargonium* plant, botanically known as *Pelargonium zonale* X *Pelargonium peltatum*, commonly referred to as Interspecific Geranium, and hereinafter referred to by the name 'Dopelbezsal'.

The new *Pelargonium* plant is a product of a planned breeding program conducted by the Inventor in Kako, Ethiopia and De Lier, The Netherlands. The objective of the breeding program is to create new freely-branching and freely-flowering *Pelargonium* plants with attractive leaf and flower coloration.

The new *Pelargonium* plant originated from a cross-pollination made by the Inventor during the winter of 2015 in Koka, Ethiopia of a proprietary selection of *Pelargonium zonale* identified as code designation PL13-000618-017, not patented, as the female, or seed, parent with a proprietary selection of *Pelargonium peltatum* identified as code designation PG13-002037-008, not patented, as the male, or pollen, parent. The new *Pelargonium* plant was discovered and selected by the Inventor as a single flowering plant from within the progeny of the stated cross-pollination in a controlled greenhouse environment in De Lier, The Netherlands in June, 2016.

Asexual reproduction of the new *Pelargonium* plant by vegetative terminal cuttings in a controlled greenhouse environment in De Lier, The Netherlands since July, 2016 has shown that the unique features of this new *Pelargonium* plant are stable and reproduced true to type in successive generations.

SUMMARY OF THE INVENTION

Plants of the new *Pelargonium* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dopelbezsal'. These characteristics in combination distinguish 'Dopelbezsal' as a new and distinct *Pelargonium* plant:

1. Upright and rounded plant habit.
2. Vigorous growth habit.
3. Freely basal branching habit.
4. Dark green-colored leaves.
5. Early and freely flowering habit.
6. Large salmon pink-colored flowers.
7. Good garden performance and high temperature tolerance.

Plants of the new *Pelargonium* differ primarily from plants of the female parent selection in the following characteristics:

1. Leaves of plants of the new *Pelargonium* do not have a discernible leaf zonation pattern whereas leaves of plants of the female parent selection have a distinct zonation pattern.
2. Flowers of plants of the new *Pelargonium* have fewer petals than flowers of plants of the female parent selection.

Plants of the new *Pelargonium* differ primarily from plants of the male parent selection in flower color as plants of the new *Pelargonium* have salmon pink-colored flowers whereas plants of the male parent selection have white-colored flowers with pink-colored spots.

Plants of the new *Pelargonium* can also be compared to plants of *Pelargonium zonale* 'Duebezpinimp', disclosed in U.S. Plant Pat. No. 27,852. In side-by-side comparisons, plants of the new *Pelargonium* differ primarily from plants of 'Duebezpinimp' in the following characteristics:

1. Plants of the new *Pelargonium* are more compact and more rounded than plants of 'Duebezpinimp'.
2. Plants of the new *Pelargonium* have smaller leaves than plants of 'Duebezpinimp'.
3. Plants of the new *Pelargonium* have smaller inflorescences than plants of 'Duebezpinimp'.
4. Flowers of plants of the new *Pelargonium* are salmon pink in color whereas flowers of plants of 'Duebezpinimp' are dark pink in color.

BRIEF DESCRIPTION OF THE PHOTOGRAPH

The accompanying colored photograph illustrates the overall appearance of the new *Pelargonium* plant showing the colors as true as it is reasonably possible to obtain in colored reproductions of this type. Colors in the photograph may differ slightly from the color values cited in the detailed botanical description which accurately describe the colors of the new *Pelargonium* plant.

The photograph is a side perspective view of a typical flowering plant of 'Dopelbezsal' grown in a container.

DETAILED BOTANICAL DESCRIPTION

The aforementioned photograph and following observations, measurements and values describe plants grown during the summer in 17-cm containers in a glass-covered greenhouse in De Lier, The Netherlands and under cultural practices typical of commercial *Pelargonium* production. During the production of the plants, day temperatures ranged from 20° C. to 30° C., night temperatures ranged from 12° C. to 20° C. and light levels averaged 135 watt/$m^2$. Plants were ten weeks old when the photograph was taken and 13 weeks old when the description was taken. In the detailed description, color references are made to The Royal Horticultural Society Colour Chart, Fifth Edition, except where general terms of ordinary dictionary significance are used.

Botanical classification: *Pelargonium zonale* X *Pelargonium peltatum* 'Dopelbezsal'.

Parentage:

*Female, or seed, parent.*—Proprietary selection of *Pelargonium zonale* identified as code designation PL130-000618-017, not patented.

*Male or pollen parent.*—Proprietary selection of *Pelargonium peltatum* identified as code designation PG13-002037-008, not patented.

Propagation:

*Type.*—By vegetative terminal cuttings.

*Time to initiate roots, summer.*—About 18 days at temperatures ranging from 22° C. to 30° C.

*Time to initiate roots, winter.*—About 21 days at temperatures ranging from 22° C. to 30° C.

*Time to produce a rooted young plant, summer.*—About 25 days at temperatures ranging from 22° C. to 30° C.

*Time to produce a rooted young plant, winter.*—About 28 days at temperatures ranging from 20° C. to 25° C.

*Root description.*—Medium in thickness, fibrous; typically greyish white in color, actual color of the roots is dependent on substrate composition, water quality, fertilizer type and formulation, substrate temperature and physiological age of roots.

*Rooting habit.*—Moderately freely branching, medium density.

Plant description:

*Plant and growth habit.*—Compact, upright and rounded plant habit; vigorous growth habit; moderate growth rate; freely branching habit with about three primary lateral branches each with about two secondary lateral branches developing per plant; densely foliated with inflorescences positioned above the foliar plane.

*Plant height, to top of foliar plane.*—About 8 cm.

*Plant height, to top of floral plane.*—About 18 cm.

*Plant width.*—About 24 cm.

*Lateral branches.*—Length: About 7 cm. Diameter: About 8 mm. Internode length: About 1 cm to 3 cm. Strength: Moderately strong. Aspect: Mostly upright. Texture and luster: Pubescent; semi-glossy. Color, developing: Close to 144A. Color, developed: Close to 199A.

Leaf description:

*Arrangement.*—Alternate; simple.

*Length.*—About 4.5 cm.

*Width.*—About 4.5 cm.

*Shape.*—Reniform.

*Apex.*—Rounded and emarginate.

*Base.*—Cordate.

*Margin.*—Lobate; sinuses medium in depth.

*Venation pattern.*—Palmate.

*Texture and luster, upper surface.*—Pubescent; semi-glossy.

*Texture and luster, lower surface.*—Smooth, glabrous; matte.

*Color.*—Developing and fully expanded leaves, upper surface: Close to N137A; venation, close to 144A. Developing and fully expanded leaves, lower surface: Close to 147B; venation, close to 147C. Zonation pattern: Not discernible.

*Petioles.*—Length: About 2.5 cm. Diameter: About 1.8 mm. Strength: Moderately strong. Texture and luster, upper and lower surfaces: Smooth, glabrous; semi-glossy. Color, upper and lower surfaces: Close to 144A.

Flower description:

*Flower arrangement*.—Large round flowers arranged in rounded hemispherical umbels arising from apical leaf axils; umbels displayed above the foliar plane on moderately strong peduncles; flowers face upright to outwardly depending on position in the umbel.

*Fragrance*.—None detected.

*Quantity of flowers*.—Freely flowering habit; about 64 flowers and flower buds per plant.

*Flowering season*.—In The Netherlands, flowering is continuous from spring through the summer; early flowering habit, plants begin flowering about eight weeks after planting.

*Flower longevity*.—Individual flowers last about five to seven days on the plant; flowers persistent.

*Flower buds*.—Length: About 7 mm. Diameter: About 7 mm. Shape: Ovoid. Texture and luster: Smooth, glabrous; matte. Color: Close to 144A.

*Umbel height*.—About 4.3 cm.

*Umbel diameter*.—About 8.5 cm.

*Flower diameter*.—About 4 cm.

*Flower depth* (*height*).—About 1.9 cm.

*Petals*.—Quantity and arrangement: About five to seven in a single whorl. Length: About 2.2 cm. Width: About 1.8 cm. Shape: Obovate. Apex: Rounded. Base: Attenuate. Margin: Sinuate. Texture and luster, upper and lower surfaces: Smooth, glabrous; matte. Color: When opening and fully opened, upper surface: Close to 49A; venation, close to 49A; color becoming closer to 65A with subsequent development. When opening and fully opened, lower surface: Close to 69A; venation, close to 65A; color becoming closer to 65B with subsequent development.

*Sepals*.—Quantity per flower: Five arranged in a single whorl. Length: About 9 mm. Width: About 2 mm. Shape: Ensiform. Apex: Apiculate. Base: Acute. Margin: Entire. Texture and luster, upper and lower surfaces: Smooth, glabrous; semi-glossy. Color, upper and lower surfaces: Close to 144A.

*Peduncle* (*umbel stem*).—Length: About 8 cm. Diameter: About 3.5 mm. Strength: Moderately strong. Aspect: Mostly upright. Texture and luster: Smooth, glabrous; semi-glossy. Color: Close to 144A.

*Pedicel* (*individual flower stem*).—Length: About 2.5 cm. Diameter: About 1.5 mm. Strength: Moderately strong. Angle: Mostly upright. Texture and luster: Smooth, glabrous; semi-glossy. Color: Close to 152D.

*Reproductive organs*.—Androecium: Stamen quantity per flower: About eleven. Filament length: About 6 mm. Filament color: Close to NN155B. Anther size: About 0.3 mm by 2 mm. Anther shape: Oblong. Anther color: Close to 169A. Pollen amount: Moderate. Pollen color: Close to 28A. Gynoecium: Pistil quantity per flower: One. Pistil length: About 7 mm. Stigma diameter: About 0.5 mm. Stigma shape: Decurrent. Stigma color: Close to 169A. Style length: About 6 mm. Style color: Close to NN155B. Ovary color: Close to 144A.

*Fruits and seeds*.—To date, fruit and seed development has not been observed on plants of the new *Pelargonium*.

Pathogen & pest resistance: To date, plants of the new *Pelargonium* have not been observed to be resistant to pathogens and pests common to *Pelargonium* plants.

Garden performance: Plants of the new *Pelargonium* have been observed to have good garden performance and to tolerate rain, wind and temperatures ranging from about 4° C. to 45° C.

It is claimed:

1. A new and distinct *Pelargonium* plant named 'Dopelbezsal' as illustrated and described.

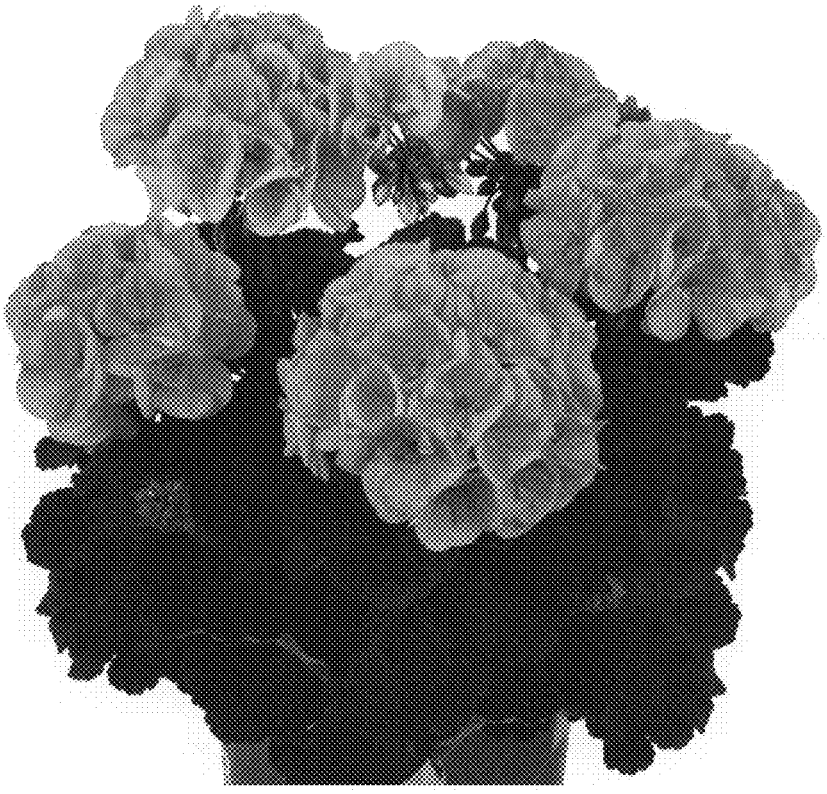

* * * * *